United States Patent
Ronen et al.

(10) Patent No.: US 9,753,968 B1
(45) Date of Patent: Sep. 5, 2017

(54) SYSTEMS AND METHODS FOR DETECTION OF ANOMALOUS ENTITIES

(71) Applicant: SparkBeyond Ltd., Zikhron-Yaakov (IL)

(72) Inventors: Amir Ronen, Haifa (IL); Meir Maor, Netanya (IL); Sagie Davidovich, Zikhron-Yaakov (IL); Ron Karidi, Herzliya (IL)

(73) Assignee: SparkBeyond Ltd., Zikhron-Yaakov (IL)

( * ) Notice: Subject to any disclaimer, the term of this patent is extended or adjusted under 35 U.S.C. 154(b) by 0 days.

(21) Appl. No.: 15/186,718

(22) Filed: Jun. 20, 2016

Related U.S. Application Data

(60) Provisional application No. 62/304,247, filed on Mar. 6, 2016.

(51) Int. Cl.
*G06N 5/04* (2006.01)
*G06F 17/30* (2006.01)
*G06N 99/00* (2010.01)

(52) U.S. Cl.
CPC ......... *G06F 17/30371* (2013.01); *G06N 5/04* (2013.01); *G06N 99/005* (2013.01)

(58) Field of Classification Search
CPC .................................................. G06N 99/005
See application file for complete search history.

(56) References Cited

U.S. PATENT DOCUMENTS

| | | | | |
|---|---|---|---|---|
| 7,281,188 B1* | 10/2007 | Bonwick | ............. | H03M 13/096 |
| | | | | 714/752 |
| 8,407,423 B2* | 3/2013 | Pelleg | ................. | G06F 12/0862 |
| | | | | 706/47 |
| 9,324,041 B2 | 4/2016 | Davidovich | ......... | G06N 99/005 |
| 2002/0120905 A1* | 8/2002 | Blaum | ................. | H03M 13/09 |
| | | | | 714/800 |
| 2005/0174853 A1* | 8/2005 | Ronen | ................ | G11C 16/3468 |
| | | | | 365/185.28 |
| 2009/0328215 A1* | 12/2009 | Arzi | ...................... | G06F 21/316 |
| | | | | 726/23 |
| 2009/0328216 A1* | 12/2009 | Rafalovich | ......... | H04L 43/0876 |
| | | | | 726/23 |
| 2011/0319746 A1* | 12/2011 | Kochba | ................ | A61B 5/0507 |
| | | | | 600/407 |

(Continued)

*Primary Examiner* — Paulinho E Smith

(57) ABSTRACT

There is provided a computer-implemented method of identifying anomalous entities in a dataset, comprising: selecting a subset of training entities from entities of at least one dataset; determining dummy tuplets of entities in the subset by applying a permutation function on real tuplets, wherein the real tuplets represent original and normal data of the at least one dataset, wherein the dummy tuplets represent anomalous data based on artificially created data not found in the original and normal at least one dataset, each one of the real tuplets and dummy tuplets comprises at least two of the training entities; analyzing the dummy tuplets and the real tuplets to identify at least one predefined characteristic relation that statistically differentiates between the real tuplets and the dummy tuplets according to a distinguishing requirement; and outputting the identified at least one predefined characteristic relation to identify a normal entity and/or an anomalous entity.

31 Claims, 5 Drawing Sheets

(56) References Cited

U.S. PATENT DOCUMENTS

| | | | |
|---|---|---|---|
| 2013/0227113 A1* | 8/2013 | Baras | H04L 41/0893 709/224 |
| 2013/0301823 A1* | 11/2013 | Baras | G06Q 50/01 379/265.02 |
| 2014/0033174 A1* | 1/2014 | Farchi | G06F 11/3676 717/124 |
| 2016/0041849 A1* | 2/2016 | Naveh | G06F 9/5088 718/104 |

* cited by examiner

SYSTEMS AND METHODS FOR DETECTION OF ANOMALOUS ENTITIES

RELATED APPLICATIONS

This application claims the benefit of priority under 35 USC 119(e) of U.S. Provisional Patent Application No. 62/304,247 filed Mar. 6, 2016, the contents of which are incorporated herein by reference in their entirety.

This application is also related to U.S. patent application Ser. No. 14/595,394, filed Jan. 13, 2015, now U.S. Pat. No. 9,324,041, titled "FUNCTION STREAM BASED ANALYSIS", assigned to the same entity, and by some of the same inventors, the contents of which are incorporated herein by reference in their entirety.

This application is also related to U.S. Provisional Patent Application No. 62/193,196, titled "SYSTEM AND METHOD FOR FEATURE GENERATION OVER ARBITRARY OBJECTS", filed Jul. 16, 2015, assigned to the same entity, and by some of the same inventors, the contents of which are incorporated herein by reference in their entirety.

This application is also related to U.S. Provisional Patent Application No. 62/193,199, titled "SYSTEMS AND METHODS FOR SECONDARY KNOWLEDGE UTILIZATION IN MACHINE LEARNING", filed Jul. 16, 2015, assigned to the same entity, and by some of the same inventors, the contents of which are incorporated herein by reference in their entirety.

BACKGROUND

The present invention, in some embodiments thereof, relates to machine learning and, more specifically, but not exclusively, to systems and methods for automatic identification of anomalous data in a dataset for use in a data mining and/or machine learning process.

Anomaly detection may be considered as a subfield in data mining and/or machine learning, that includes the goal of identifying, for example, items, events, observations that do not conform to an expected pattern within a dataset. The anomalous items may correspond a solution to a problem, for example, detecting activity indicative of bank fraud, detection of a structural defect, detection of a medical problem, or detection of errors within text.

SUMMARY

According to an aspect of some embodiments of the present invention there is provided a computer-implemented method of identifying anomalous entities in a dataset, comprising: selecting a subset comprising a plurality of training entities from a plurality of entities of at least one dataset; determining a plurality of dummy tuplets of entities in the subset by applying a permutation function on a plurality of real tuplets, wherein the real tuplets represent original and normal data of the at least one dataset, wherein the dummy tuplets represent anomalous data based on artificially created data not found in the original and normal at least one dataset, each one of the plurality of real tuplets and dummy tuplets comprises at least two of the plurality of training entities; analyzing the plurality of dummy tuplets and the plurality of real tuplets to identify at least one predefined characteristic relation that statistically differentiates between the real tuplets and the dummy tuplets according to a distinguishing requirement; and outputting the identified at least one predefined characteristic relation to identify at least one of a normal entity and an anomalous entity of the at least one dataset or in a newly received dataset.

Optionally, the method further comprises calculating a first classifier that identifies the at least one predefined characteristic relation that statistically differentiates between an anomalous entity and a normal entity; and calculating a second classifier for detecting at least one of an anomalous entity and a normal entity in the at least one dataset or in the newly received dataset based on the at least one predefined characteristic relation identified by the first classifier.

Optionally, the plurality of training entities represent certain values assigned to variables, wherein each of the real tuplets comprises a tuplet of variables. Optionally, the dataset includes a plurality of data instance each associated with at least one of the parameters having assigned values represented as entities, wherein each of the real tuplets comprises at least two different parameters.

Optionally, the dataset includes a plurality of data instances each including at least one entity, wherein the dataset is represented as a table, wherein each row of the table represents a respective data instance and each column of the table represents a respective entity, wherein the real tuplets includes at least two columns of the table. Optionally, the dataset comprises raw data that includes normal data instances and unknown anomalous data instances. Optionally, the permutation function is applied to at least one columns of the table to permute the entities of the rows of the column, such that the dummy tuplets includes for each row at least original entity and at least one permuted entity.

Optionally, the permutation function samples entities from the entities of the real tuplets according to a proportion requirement defining the proportion of real pairs to dummy pairs.

Optionally, the training entities include objects of arbitrary types. Optionally, the arbitrary types are members selected from a set consisting of: time series, vector, map, graph, text, and tree. Optionally, the training entities include complex data structures storing multiple parameters.

Optionally, the predefined characteristic relation is associated with values outputted by at least one function that processes each entity of the real tuplets.

Optionally, the predefined characteristic relation is identified based on at least one combination function created by selecting a function group of building block functions adapted for processing the entities of the real tuplets, and combining members of the function group to create a set of combination functions each created from at least two members of the function group.

Optionally, the method further comprises selecting the characteristic relation by: applying each member of the set of combination functions to each real tuplet to create a set of results, analyzing the set of results to identify a correlation between the at least one member of the set of combination functions and a target variable for analysis of the real tuplets according to a correlation requirement, wherein the characteristic relation is selected based on the identified at least one member of the set of combination functions.

Optionally, analyzing comprises applying a function to extract dummy feature-values from each of the plurality of dummy tuplets and real feature-values each of the plurality of real tuplets, and applying a classifier to statistically differentiate between the dummy feature-values and the real feature-values to identify the at least one characteristic relation.

Optionally, the method further comprises applying each of a plurality of predefined characteristic relations to the real tuplets to extract a first set of features representing realfeature-values; applying each of the plurality of predefined characteristic relation to the dummy tuplets to extract a second set of features representing dummy-feature-values representing anomalous entities; and identifying the at least one predefined characteristic relation that statistically differentiates between the first set and the second set.

Optionally, the method further comprises calculating an anomalous entity sub-score for each of the dummy tuplets based on the identified at least one predefined characteristic relation applied to each respective dummy tuplet, and calculating an anomalous score for an identified anomalous data entity by aggregating sub-scores of dummy tuplets associated with the respective anomalous data entity.

Optionally, the method further comprises applying the identified at least one predefined characteristic to the real tuplets to extract a first set of features representing real-feature-values; applying the identified at least one predefined characteristic to the at least one entity of the dummy tuplets and to at least one entity of the real tuplets, to extract a second set of features representing dummy-feature-values representing anomalous entities; and calculating a classifier to identify at least one of a normal entity and an anomalous entity according to first set and the second set.

Optionally, the permutation function is a random permutation function.

Optionally, the permutation function is based on a predefined statistical distribution designed to capture a representative permutation sample to reduce computations resources as compared to computing all possible permutations.

Optionally, the method further comprises iterating the determining and the analyzing by constraining a plurality of real tuplets of the subset at each iteration by applying a set-of-rules, and applying the permutation function according to the set-of-rules to respect the constraining to determine the plurality of dummy tuplets. Optionally, the method further comprises storing the at least one identified characteristic relation for each iteration, and wherein the set-of-rules applied in a next iteration include the identified at least one characteristic such that applying the permutation function according to the set-of-rules retains the stored at least one identified characteristic relation. Optionally, the set-of-rules defines at least two real entities included the in the plurality of real tuplets which retain their relative positions, such that the at least two real entities are permuted together by the applied permutation function.

Optionally, the subset is selected according to a statistical estimate based on an estimated amount of anomalous entities in the at least one dataset such that applying the identified at least one predefined characteristic relation to each pair of the plurality of real tuplets is statistically significant according to a correlation requirement.

Optionally, the at least one predefined characteristic relation is applied between real tuplets of entities of the same data instance of the subset.

Optionally, the at least one predefined characteristic relation is selected by: applying a function to each real tuplets to calculate a set of first results; generating a set of characteristic relations wherein each characteristic relation includes the function for application to another real tuplets to calculate a second result, and at least one condition defined by at least one respective member of the set of first results applied to the second result; applying each characteristic relation of the generated set of characteristic relations to each instance of a second subset selected from the at least one dataset to generate a set of extracted features; selecting a subset of characteristic relations from the set of characteristic relations according to a correlation requirement between at least one classification variable and each respective member of the set of characteristic relations; and designating the selected subset of characteristic relations at the identified at least one predefined characteristic relation.

Optionally, the method further comprises presenting at least one of the identified at least one predefined characteristic relations on a display; receiving a manual a selection of at least one of the presented predefined characteristic relations from a user via a user interface; and wherein outputting comprises outputting the at least one manually selected predefined characteristic relations.

According to an aspect of some embodiments of the present invention there is provided a system for identifying anomalous entities in a dataset, comprising: a data interface for communicating with a storage unit storing thereon at least one dataset; a program store storing code; and a processor coupled to the data interface and the program store for implementing the stored code, the code comprising: code to select a subset comprising a plurality of training entities from a plurality of entities of at least one dataset; code to determine a plurality of dummy tuplets of entities in the subset by applying a permutation function on a plurality of real tuplets, wherein the real tuplets represent original and normal data of the at least one dataset, wherein the dummy tuplets represent anomalous data based on artificially created data not found in the original and normal at least one dataset, each one of the plurality of real tuplets and dummy tuplets comprises at least two of the plurality of training entities; code to analyze the plurality of dummy tuplets and the plurality of real tuplets to identify at least one predefined characteristic relation that statistically differentiates between the real tuplets and the dummy tuplets according to a distinguishing requirement; and code to output the identified at least one predefined characteristic relation to identify at least one of a normal entity and an anomalous entity the at least one dataset or in a newly received dataset.

According to an aspect of some embodiments of the present invention there is provided a computer program product comprising a non-transitory computer readable storage medium storing program code thereon for implementation by a processor of a system for identifying anomalous entities in a dataset, comprising: instructions to select a subset comprising a plurality of training entities from a plurality of entities of at least one dataset; instructions to determine a plurality of dummy tuplets of entities in the subset by applying a permutation function on a plurality of real tuplets, wherein the real tuplets represent original and normal data of the at least one dataset, wherein the dummy tuplets represent anomalous data based on artificially created data not found in the original and normal at least one dataset, each one of the plurality of real tuplets and dummy tuplets comprises at least two of the plurality of training entities; instructions to analyze the plurality of dummy tuplets and the plurality of real tuplets to identify at least one predefined characteristic relation that statistically differentiates between the real tuplets and the dummy tuplets according to a distinguishing requirement; and instructions to output the identified at least one predefined characteristic relation to identify at least one of a normal entity and an anomalous entity the at least one dataset or in a newly received dataset.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
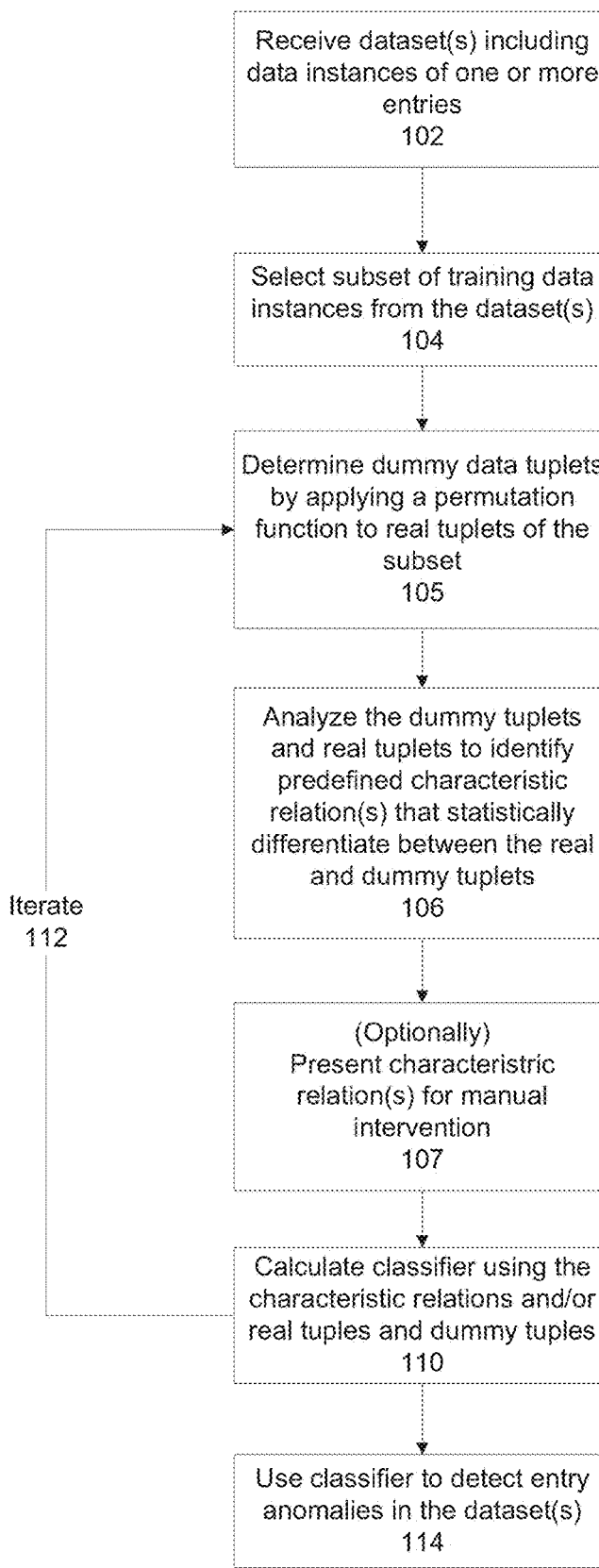
FIG. 1A is a flowchart of a process that automatically identifies characteristic relations that identify anomalous entities in a dataset, in accordance with some embodiments of the present invention.

The present invention, in some embodiments thereof, relates to machine learning and, more specifically, but not exclusively, to systems and methods for automatic identification of anomalous data in a dataset for use in a data mining and/or machine learning process.

An aspect of some embodiments of the present invention relates to systems (e.g., a processing unit executing code instructions stored in a memory) and/or methods (e.g., implemented by the processing unit) that automatically process one or more datasets each including data instances comprising one or more entities, to identifies characteristic relations that are used to identify anomalous and/or normal data instances. Most or all values of the data instances in the dataset represent a normal set of values. One or more unknown data instances may represent anomalies, optionally a relatively small number of data instances relative to the dataset, for example, about 0.1%, or about 0.5%, or about 1%, or about 1.5%, or about 2%, or other smaller, intermediate, or larger values. The systems and/or methods permute some of the entities of each data instance in the dataset relative to other intact (i.e., non-permuted, original) entities of the same data instance, to create a new data instance which includes a portion of normal (i.e., real) entity values and another portion of dummy (e.g., fake, non-normal) entity values. Each newly created dummy data instance (or tuple) represents anomalous data. Characteristic relations (e.g., functions, extractable features) that statistically significant differentiate between real data instances (e.g., real tuplets) and dummy data instances (e.g., dummy tuplets) are identified, for based on clustering methods, supervised feature search methods, and other statistical methods. The identified characteristic relations may be used to identify normal data instances and/or an anomalous data instances in the dataset and/or in a newly received data instance and/or dataset. The identified characteristic relations may be used to identify normal and/or anomalous data entries in a data instance, for example, an otherwise normal data instance may include anomalous data entries, for example, a medical record of a patient containing different types of tests (e.g., blood, imaging, urine, stool) may be analyzed to detect an abnormal blood test.

A classifier may be calculated based on the real data instances of the dataset (or subset thereof, representing normal data values) and the created dummy data instances (representing anomalous data). The classifier may detect an anomalous data instance (which may include one or more anomalous entities) in the original dataset and/or in a new dataset, and/or for newly received data instances. The creation of the dummy tuplets artificially increases the proportion of anomalous data to reach a statistically significant level, which allows calculation of a classifier that is able to differentiate between normal and anomalous data with improved statistical significance. The features may be used to calculate the classifier, for example, the predefined characteristic relations are respectively applied to the real data instances (or tuplets) to extract real feature values, and to the dummy data instances (or tuplets) to extract dummy feature values. The real feature values and dummy feature values are used to calculate the classifier to detect anomalous entities (e.g., anomalous data instances). The classifier may be used to detect normal or anomalous data instances, for example, a patient may be identified as sick based on detected anomalous entities in their medical record.

The data instances of the dataset may include one or more entities each representing a certain value of a parameter and/or variable. The data instances each have respective values assigned to corresponding variables. For example, each data instance may represent demographic information for a respective citizen. Corresponding variables may include age, gender, and income. Each citizen (i.e., data entity) is associated with its own respective values for the parameters. For example, for John Smith, age=35, gender=male, and income=$100000. For Maria Jones, age=75, gender=female, and income=$24000.

As used herein, the term tuplet (e.g., pair, triplet, or other n-tuplet where n>=2) refers to two or more variables of the data instances, optionally two or more entities. For example, for data instances representing demographic data of citizens, where the age, gender, and income are stored for each citizen, the tuplet (e.g., pair) may include the age and gender, or the age and income, or the gender and income.

The dataset may be represented as a table (or other equivalent data structures), where each row represents a respective data instance and each column represents a respective entity (e.g., variable of the data instances, storing values of the respective variable of the respective data instance).

As described herein, the term tuplet (e.g., pair, triplet, or other n-tuplet with at least two members), such as the characteristic relation identified between members of the tuple, may represent two or more columns of the table (i.e., the characteristic relation identified between the two or more columns), or other equivalent data structures.

Optionally, the data instances include objects of arbitrary type or defined data type, optionally complex objects which may each include multiple members (or nested complex objects), for example, time series, vectors, maps, graphs, text, sets and trees. In this manner, the systems and/or methods (e.g., implemented by the processing unit) described herein may calculate the classifier to detect the anomalous data instance regardless of the underlying data implementation.

As used herein, the term feature-value means the output of a function and/or predefined characteristic relation applied to two or more entities of a data instance.

Optionally, the classifier is calculated based on one or more predefined characteristic relations between two or more entities within each data instance. The predefined characteristic relations may be extracted by a function applied to the two or more entities of each data instance. The function may output an extracted feature-value based on the predefined characteristic relation. For example, when each data instance represents height and weight (i.e., as a tuplet of entities) of patients, an example predefined characteristic relation is the body mass index (BMI) calculated from the height and weight.

The function may be selected such that the outputted feature-value has a relatively high correlation when extracted from entities within a real (i.e., normal) data instance, for example, relative to a correlation requirement. Alternatively or additionally, the function is selected such that the outputted feature-value has a relatively low correlation when extracted from entities within a dummy (e.g., the created) data instance, for example, relative to a correlation requirement. In this manner, the function is selected to statistically differentiate between the normal and anomalous entities according to the distinguishing requirement.

Optionally, an anomalous score is calculated for the identified anomalous data instances by aggregating subscores of dummy tuplets associated with the respective anomalous data instance. Anomalous entity sub-scores may be calculated based on the created anomalous data. For example, a data instance with a greater number of anomalous entities (e.g., as determined by the predefined characteristic relations) may have a relatively higher anomalous score than another data instance with fewer anomalous entities. The anomalous score may define the degree of anomalous entities associated with the created anomalous data instance. The classifier may be calculated based on the calculated anomalous entity sub-scores associated with respective anomalous entities of data instances. The anomalous entity sub-scores may improve the ability of the classifier to detect anomalous data instances (and/or anomalous entities) having relatively higher anomalous scores (calculated by aggregating the anomalous entity sub-scores) representing data with relatively higher anomaly level (e.g., which may representing riskier data).

The systems and/or methods (e.g., implemented by the processing unit) described herein improve the process of automatic detection of anomalous entities in a dataset, by creating anomalous data from normal data instances, identifying characteristic relations that statistically differentiate between the anomalous entities and the normal entities, and optionally training the classifier to identify the anomalous and/or normal data instances based on the created anomalous data and the identified characteristic relations. The anomalous data instances may be detected in a dataset that includes arbitrary objects, independently of the actual object implementation type, and/or without requiring knowledge of the actual object type. The data instances of the dataset may be processed in their raw form, which may be unclassified, not necessarily requiring classification of the raw data for processing, and/or particular formatting. It is noted that labeling of the data and/or formatting of the entities of the data instances may be performed as part of the processes described herein, but is not necessarily required in advance. In this manner, the classifier may use existing datasets of normal values to detect anomalous data instances when the available real anomalous data (e.g., based on real data collected from observed anomalous instances) may be insufficient to train a classifier to statistically differentiate between normal data and anomalous data (e.g., according to a differentiation requirement). For example, in cases where anomalous data is, limited, rare, and/or non-existent.

The systems and/or methods described herein generate a new set of data (which may be stored locally and/or remotely, or transmitted to another server) which includes the permuted entities, for example, the second dataset that includes real entities and dummy entities. Moreover, the systems and/or methods described herein may calculate a new classifier that identifies anomalous entities and/or anomalous data instances in the dataset. The permuted entities and/or dummy data and/or calculated classifier may be implemented by data mining and/or machine learning processes for improving the data mining and/or machine learning process, such as in terms of improvements in anomalous entity detection accuracy, improvements in computing resources utilization, and/or improvements in time taken to perform the anomalous entity detection.

The systems and/or methods described herein improve an underlying technical process within the technical field of data mining and/or machine learning. The technical problem addressed is that of identifying characteristic relations that statistically differentiate between normal entities and anomalous entities. Another addressed technical problem relates to calculating a classifier that improves accuracy of detection of anomalous entities in a dataset, optionally in a dataset that includes objects of an arbitrary data type. In such dataset, anomalous entities may not be identifiable using other automated methods, and/or manual methods. The systems and/or methods described herein allow for automated detection of anomalous and/or normal entities, which improves system performance (e.g., in terms of reduced processing tie), for example, in comparison to cases in which other machine learning methods may not be able to detect anomalous entities (e.g., lack of training data) and/or in comparison with manual methods (e.g., unreasonable for a human to manually label a large amount of data and/or complex data).

The systems and/or methods described herein improve performance of the computing unit executing the code instructions to identify characteristic relations that statistically differentiate between normal entities and anomalous entities and/or code that creates the classifier that identifies anomalous entities in the dataset and/or in new data instances, by creating a new dataset that includes dummy entities and real entities, which improves improve computing resource utilizing (e.g., processor utilization and/or storage requirements), for example, in comparison to other computing system that require a larger set of data (e.g., the system described herein may use a relatively smaller set of normal data) and/or manual labeling of data (e.g., the system described herein does not require manual data labeling), and/or additional computation time and/or additional processing resources and/or larger storage capacity.

The systems and/or methods described herein provide a unique, particular, and advanced technique of identifying characteristic relations that statistically differentiate between normal entities and anomalous entities, and optionally calculating a classifier to detect anomalous and/or normal entities in a dataset. The systems and/or methods described herein process data which may be organized in a specific manner, namely as data instances (described herein), to generate other new data which may be organized in a specific manner, namely a second dataset that includes real entities and dummy entities (as described herein).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term classifier (or statistical classifier) broadly means a predictive model and/or classification machine learning model, for example, a statistical classifier, a regression function, a look-up table, decision tree learning, artificial neural networks, and Bayesian networks. The classifier may be a symbolic classifier.

As used herein, the term function means a relation between inputs and outputs such that each input is related to one output. The function performs an operation on the input(s) to generate the output(s), for example, a mathematical calculation, and/or other data processing methods such as data analysis. Functional may be mathematical functions, and/or functions designed to process data, such a numeric and/or non-numeric data. Examples of functions include: a function that operates on text and returns the sentiment of the text (e.g., positive, negative, or neutral), a function that converts a string to upper case, and/or a function that performs a mathematical operation on numerical data. The term function and (predefined) characteristic relation may sometimes be interchanged. For example, the (predefined) characteristic relation may be a function.

As used herein, the term tuple, or one or more tuplets, is not necessarily limited to two entity columns when the data instances are stored as a table (or other representations corresponding to columns and tables), and may represent other tuplets representing greater numbers of entities, for example, triple, quadruple, quintuple, sextuple, septuple, octuple, and greater numbers.

As used herein, the term tuplet refers to tuplets of columns when the data instances are stored as a table (or other representations corresponding to columns and tables).

As used herein, the term data instances and entities are sometimes interchangeable. For example, anomalous entities and/or anomalous data instances may be detected in the dataset by the described system and/or method.

Figure 1B:
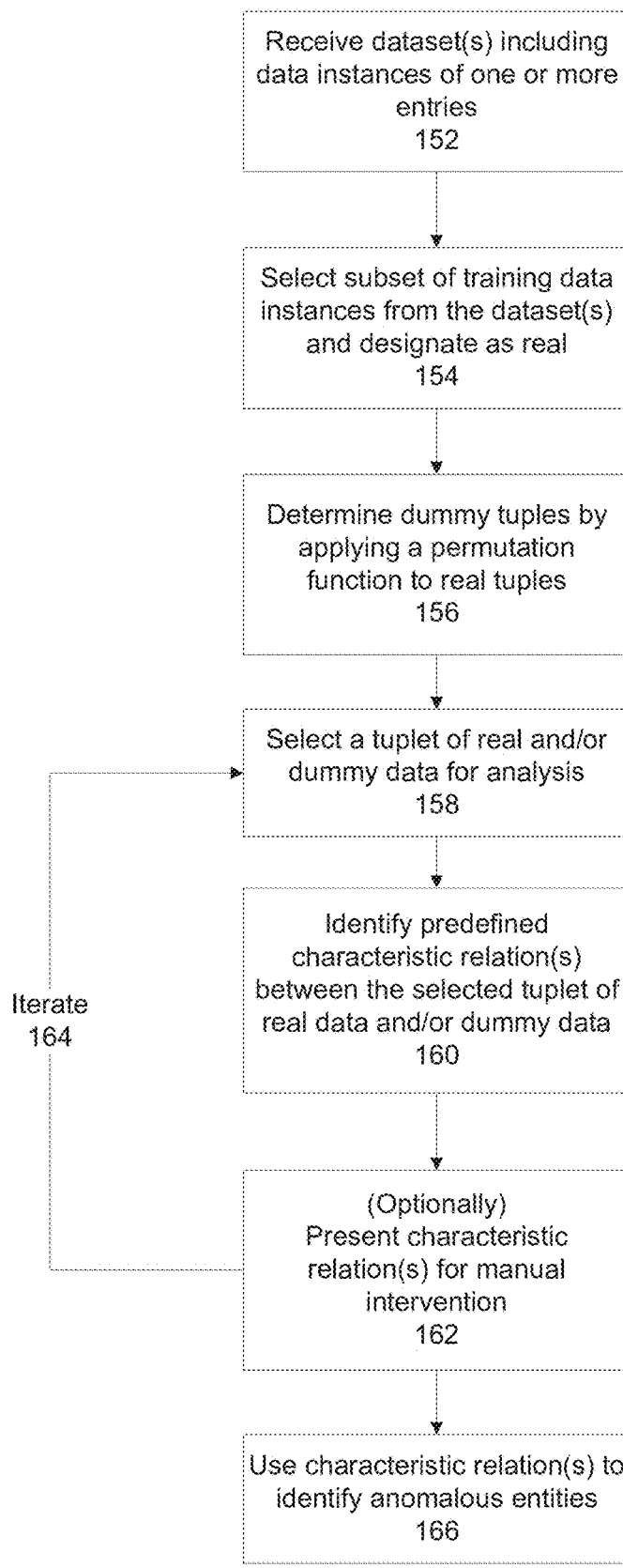
FIG. 1B is a flowchart of a process that automatically identifies characteristic relation(s) of the dataset, in accordance with some embodiments of the present invention.
Figure 1C:
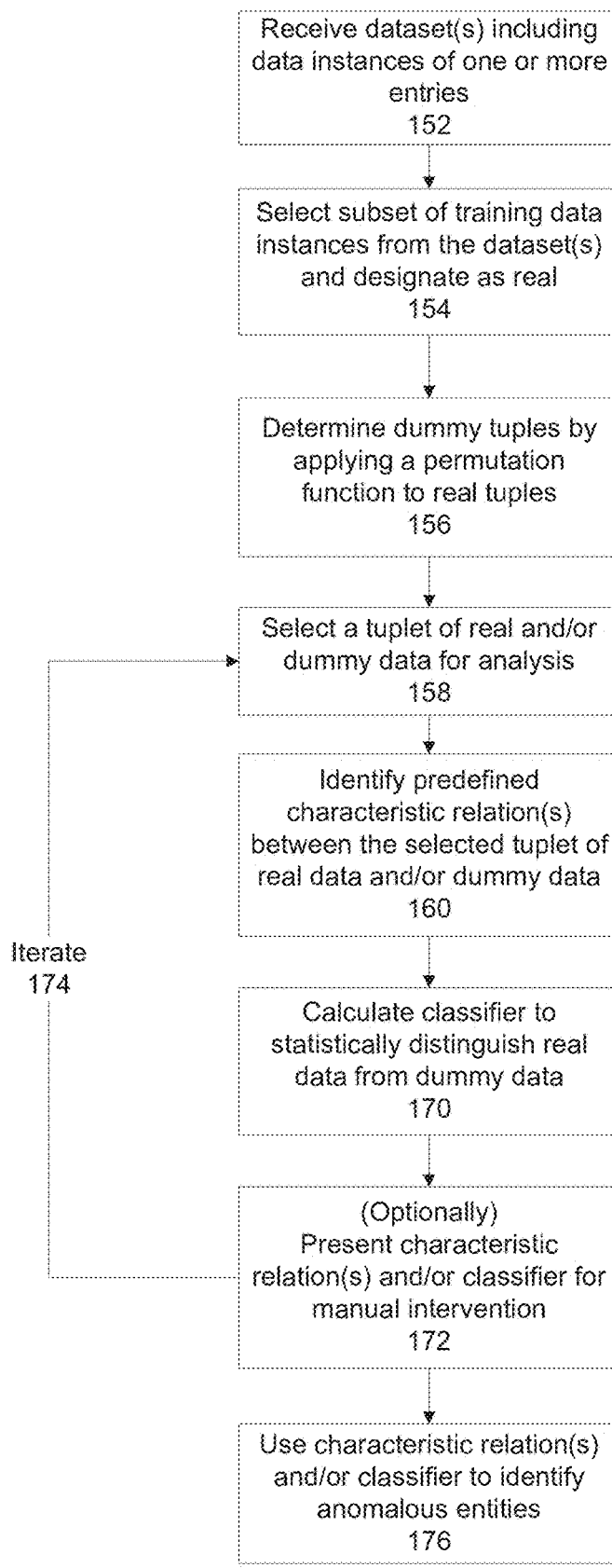
FIG. 1C is a flowchart of a process that automatically calculates a classifier and/or identifies characteristic relations of the dataset for identifying anomalous entities, in accordance with some embodiments of the present invention.
Figure 2:
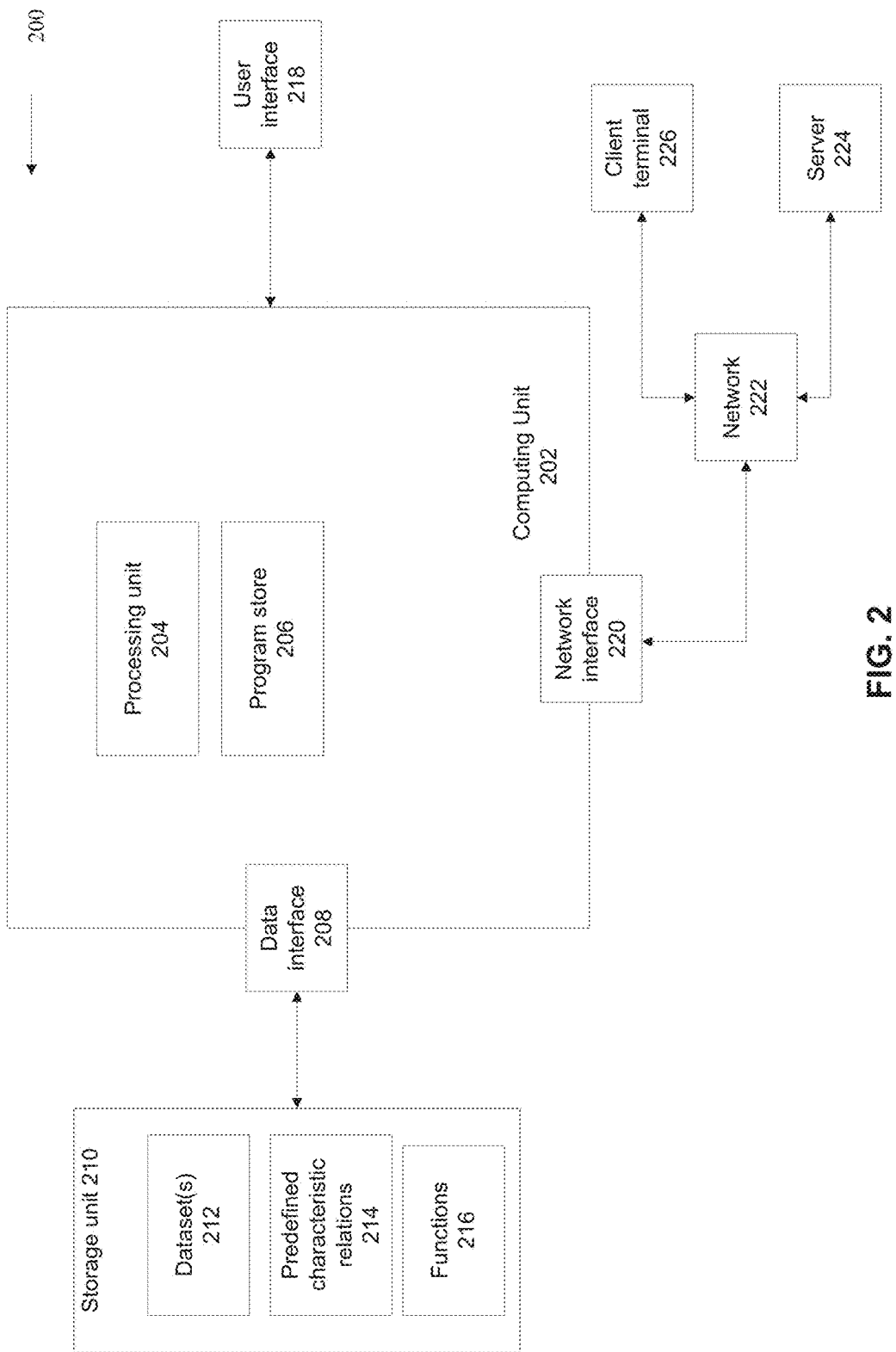
FIG. 2 is a diagram of components of a system that automatically identifies characteristic relations that identify anomalous entities in a dataset, in accordance with some embodiments of the present invention.

Reference is now made to FIGS. 1A-C, which is a flowchart of a process that automatically identifies characteristic relations that statistically differentiate between normal entities and anomalous entities and optionally calculates a classifier to identify anomalous and/or normal entities in a dataset, in accordance with some embodiments of the present invention. Reference is also made to FIG. 2, which is a block diagram of components of a system 200 that automatically creates dummy entities by applying a permutation function to at least two real entities of a dataset, identifies characteristic relations that statistically differentiate between normal entities and anomalous entities, and optionally computes the classifier based on the dummy entities and the real entities, for detection of anomalous and/or normal entities (e.g., data instances) in the dataset and/or based on new data instances and/or a new dataset, in accordance with some embodiments of the present invention. The acts of the method described with reference to FIGS. 1A-C may be implemented by system 200 of FIG. 2, optionally by a computing unit 202 that includes a processing unit 204 that executes code instructions stored in a memory 206 (e.g., program store) based on the described acts of FIGS. 1A-C.

System 200 includes computing unit 202, for example, a personal computer, a mobile device (e.g., Smartphone, Tablet), a wearable device (e.g., computing glasses, watch computer), and/or a server. Computing unit 202 includes processing unit 204, for example, a central processing unit (CPU), a graphics processing unit (GPU), field programmable gate arrays (FPGA), digital signal processor (DSP), and application specific integrated circuits (ASIC). Processing unit 204 may include one or more processors (homogenous or heterogeneous), which may be arranged for parallel processing, as clusters and/or as one or more multi core processing units. Computing unit 202 may include multiple computers (having heterogeneous or homogenous architectures), which may be arranged for distributed processing, such as in clusters.

Computing unit 204 may be implemented, for example, as a server (e.g., providing services to one or more client terminals over a network connection via a network interface 220), as a web server (e.g., providing service to clients terminals using a web browser), and/or a client running locally stored code. Computing unit 204 may be implemented as a hardware component (e.g., standalone computing unit), as a software component (e.g., implemented within an existing computing unit), and/or as a hardware component inserted into an existing computing unit (e.g., plug-in card, attachable unit). The server implementation may provide services to client terminals by providing software as a service (SAAS), providing an application that may be installed on the client that communicates with the server, and/or providing functions using remote access sessions.

Computing unit 202 includes memory (e.g., program store) 206 storing code implementable by processing unit 204, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Computing unit 202 includes a data interface 208 for communicating with a storage unit 210, which may be installed within computing unit 202, as an external device (e.g., accessible via a local connection), and/or located on a remote server 224, accessible over a network 222 via a network interface 220 (which may be integrated with data interface 208). Storage unit 210 may be implemented, for example, as a memory, a hard-drive, an optical disc, a storage unit, an interface to a remote storage server, and interface to a cloud server, and/or other storage units.

Computing unit 202 may include a user interface 218 allowing the user to enter data and/or outputting data to the user, for example, one or more of: a display, a touch screen, a keyboard, a mouse, and voice activated interface.

At 102, a dataset is received and/or designated. Dataset 212 may be stored on storage unit 210, accessible by processing unit 204 using data interface 208 (e.g. received from a sensor or other device performing measurements), and/or retrieved from a remote server 224 and/or uploaded by a user using a client terminal 226 over network 222. Designation may be performed manually by a user (using user interface 218), and/or automatically by code, and/or based on a file defining system configuration parameters. Dataset 212 may be designated from a larger collection of data.

Dataset 212 may includes multiple data instances, each including a set of objects of arbitrary types, each object assigned one or a set of values. Each data instance represents an observation that may be predicted or classified. Optionally, the training data set includes raw data, for example, generated as an output of a sensor (or other measurement device), and/or generated as an output of a computer process implemented by code. Optionally, the raw data instances are unclassified.

Dataset 212 includes data instances and/or entities representing normal values (i.e. not anomalous entities) and may include anomalous entities. The anomalous data instances and/or anomalous entities may be unknown.

Each object is represented by a data structure, optionally a complex data structure storing multiple variables. The data structure of each object may be of an arbitrary type, which does not necessarily need to conform to a specific format for processing by the systems and/or methods described herein. Objects may be, for example, of complex types: time series, vector, map, graph, and tree. Objects may be, for example, of simple types: integer, real number, string, categorical (i.e., set), and Boolean. It is noted that the complex types may be built from the simple types.

Dataset 212 may include objects which describe, for example, events, bids, potential client characteristics, sensor readings, log records, and/or any other set of records numerical and/or any textual records which reflect events and/or measurements, and optionally one or more event and/or measurement outcomes, estimations or evaluations (which may be used as labels for the data objects for training a classifier, as described herein).

Dataset 212 may be stored, for example, as a table, matrix, and/or database, with each row representing respective data instances, and each column representing objects.

The data instances may be represented mathematically as $D=(D1, \ldots, Dn)$. $Di$ (e.g., a row) may include columns $Di=(Di1, \ldots Dik)$. Each $Dij$ may represent an object as an entity. Each data instance may include one or more entities.

It is noted that the dataset may be generated from raw data, for example, from obtaining complex objects from an operational system, an online document store, and/or by joining data together (e.g., joining tables). Raw data (used as the dataset, or used to generate the dataset) may be stored in tabular form (or other corresponding representation), optionally in multiple interlinked tables, for example, in relational databases. In one example, operational systems may use object oriented data structures (which may be used to create the dataset) where complex objects have various interlinks between them. A flat form of the object oriented data structures may be created (e.g., by code having instructions to perform such conversion) before analysis described herein is performed, or alternatively, the object oriented data structures are processed using existing forms or other modified forms. Data objects which do not have a 1-1 relationship with a primary table (or other data structure) may be joined, for example, using an aggregated method for each joined column. For example, aggregation of historical data (e.g., stock prices and respective dates) may be performed by creation of a time series.

Exemplary methods of automatic joining of data to create an enhanced training dataset are described with reference to U.S. Patent Application No. 62/193,199. The method of U.S. Patent Application No. 62/193,199 may be used to join multiple tables and/or files of relational data to create a set of complex objects, where each object may include primitive types and/or sets of primate types, for example, time series or other sets of other objects.

At 104, a subset of training entities is selected from entities of one or more datasets (e.g., dataset(s) 212 stored in storage unit 210. The subset may include data instances (each data instance including entities) selected from the dataset. The subset may include a portion of the data instances (e.g., when the dataset is too large to be processed in its entirety within a reasonable time and/or using available computational resources), or the entire dataset (e.g., when the dataset is small enough to be processed in its entirety within a reasonable time and/or using available computational resources).

The subset may be randomly selected, for example, based on a random sample of entities.

The subset may be selected according to a statistical estimate, such as a statistical sample representing the dataset. The statistical estimate (e.g., sample size, which entities to select) may be based on an estimate amount (e.g. absolute number, relative number, percentage) of anomalous entities in the dataset. The actual amount of anomalous entities in the dataset may be unknown (e.g., when the dataset represents raw data, such as unprocessed measurements).

The statistical estimate may be based on the assumption that the subset representing the dataset includes a significantly low amount of anomalous entities. The statistical estimate may be selected such that applying the identified predefined characteristic relation to each real tuplet (e.g., as discussed herein) is statistically significant according to a correlation requirement. The correlation requirement may be selected to account for the presence of anomalous entities in the subset, such that the anomalous entities are not detectable when the identified predefined characteristic relation is applied to the entity tuplets (e.g., represented as tuplets of columns) of the subset. For example, in the case where the subset includes 99 normal entities and 1 anomalous entity, the correlation requirement may be selected such that the 1 anomalous entity is not detectable. For example, the value obtained by applying the characteristic relation to tuplets that include the anomalous entity falls within the statistical distribution defined as representing normal values. In this manner, even when the subset includes anomalous entities, the subset may be estimate to include entities representing normal value.

At 105, one or more dummy tuplets are determined in the subset by applying a permutation function on one or more entities (e.g., columns) of the real data. The dummy tuplets are created based on the original values obtained from the dataset. The dummy tuplets are designed to represent anomalous entities, by including the real original data, but reorganizing the real original data in a way that is different than the original data, and therefore unexpected.

The permutation function may be applied to corresponding entities from each of the data instances, for example, when the data instances are stored in a table, with each row representing a data instance and each column representing an entity, the permutation function may be applied to one or more columns of the table. The same permutation function may be applied to all selected entities (e.g., all columns), or different permutation functions may be applied to different selected entities (e.g., different permutation functions for different columns).

Optionally, the permutation function is applied to some of the entities of each data instance (and not applied to the other entities) such that the created dummy tuplets correspond to one or more original entities of each data instance.

Optionally, the permutation function is applied to some data instances (and not applied to other data instances). The proportion of data instances and/or data entities undergoing permutation may be selected. The data instances (and/or data entities) which the permutation function is applied to may be selected, for example, based on a predefined proportion parameter, for example, a percentage of the total number of data instances (and/or data entities), for example, 10%, 20%, 50%, or other percentage, or other method. The predefined proportion parameter may be manually selected by the user, obtained from stored system settings, and/or automatically determined by code. The method of applying the permutation function based on the predefined proportion parameter may be defined, for example, randomly (e.g., randomly select 10% of the data instances and apply the function to the selected data instances) or sequentially (e.g., apply the function to the first 10% of data instances).

Optionally, the original data instances and/or data entities are tagged (e.g., by adding another column to the data instances, adding another data entity to the data instances, using metadata) to indicate that the data is real, i.e., the original data. Optionally, the dummy tuplets and/or the data instances including the dummy tuplets are tagged to indicate that the data is fake, i.e., created using the permutation function.

Optionally, the permutation function is a random permutation function. The random permutation function may process corresponding entities of data instances (e.g., a column of data) by randomly mixing the location of the data instances. For example, the order of the entities in each column may be randomly permuted, for example, the original order may be {1, 2, 3, 4, 5}, and the permuted order may be {4, 1, 5, 3, 2}.

Optionally, the permutation function is based on a predefined statistical distribution designed to capture a representative permutation sample to reduce computations resources as compared to computing all possible permutations. For example, when the number of entities being permuted is 5, the total number of possible permutations is 5!, or 120. The total number of permutations grows drastically with the number of entities. It may not be possible or desirable to use all 120 possibilities. The permutation(s) may be selected based on statistical methods according to the most statistically significant permutation(s).

The permutation function may be based on an independent sample of each entity in the original dataset (i.e., larger than the selected subset of the dataset). For example, when an entity appears in the dataset with a frequency of 20%, the permutation function may the corresponding entity to 20% of the entities undergoing permutation (e.g., in the column).

Optionally, a check is performed on the dummy tuplets to verify that the created dummy tuplets are not the same as the original data, i.e., that the created dummy tuplet is not the same as another existing real tuple.

At 106, the dummy tuplets and the real tuplets are analyzed to identify predefined characteristic relation(s). Each real tuplet represents original data of the subset (i.e., of the original dataset). The predefined characteristic relations that statistically differentiate between the real tuplets and the dummy tuplets according to a distinguishing requirement may be identified, for example, based on a statistical certainty of at least 90%, or at least 80%, or other values and/or other requirements. The predefined characteristic relations may be identified by calculating a first statistical classifier that statistically differentiates between the real tuplets and the dummy tuplets. Another second classifier, as described with reference to block 110, may be calculated to differentiate between real data instances (and/or tuples and/or entities) and dummy data instances (and/or tuples and/or entities) based on the predefined characteristic relations identified by the first statistical classifier.

Each one of the real tuplets includes two or more columns of the training entities, for example the term tuplet may be interchanged with the term triplet which includes three of the training entities, or interchanged with the term quintuplet which includes five of the training entities.

In mathematical terms, the entities and/or data instances may be assumed to follow an unknown distribution represented by Q. Let Q' be an independent distribution on the supports of Q. The predefined characteristic relation is based on identified functions (e.g., composition functions) that separate Q from Q' according to the distinguishing requirement. The predefined characteristic relation uncovers hidden symbolic dependencies in the dataset.

The predefined characteristic relation(s) may be stored in a predefined characteristic relations repository 214, which may be stored on storage unit 210 and/or at another location. The predefined characteristic relations may be dynamically created (e.g., as described herein) and/or may be retried from a set of stored characteristic relations which may have been manually defined by a user and/or automatically created by code.

As used herein, the term real means the original data as provided within the dataset. As used herein, the term dummy means data which differs from the original data provided within the dataset, which may be derived from the original data, for example, by a permutation function as described herein. For example, {1,2,3,4} is the original dataset representing real data. When the dataset is permuted as described herein, dummy data is created, for example, {1,2, 4, 3}. Dummy tuplets (as described herein) represent artificially created data (e.g., data instances) not found in the original subset (i.e., the original dataset).

The predefined characteristic relation may be applied directly to values of the entities of the real tuplet without application of the function and/or may be applied to values calculated by the function(s), for example, to compare the value of the entities and/or function outputs, for example, whether values of the entities and/or function outputs are equal to each other, whether one value is larger than the other, and whether a value of one entity and/or function output is included within the other entity and/or function output (i.e., the other entity is a set of values, and/or the function outputs a set of values).

The predefined characteristic relation may be identified in association with one or more function that processes each entity of the real tuplets. The predefined characteristic relation may be applied based on each function applied to each entity of the real tuple, for example, the characteristic relation may compare the value outputted by the function applied to the first entity of the tuplet with the value outputted by the function applied to the second entity of the tuple. The function receives as input the values of the entities of each respective tuple, and outputs an output value. For example, the function is X+Y−Z, where X represents the first entity in the triplet, Y represents the second entity in the triplet, and Z represents the third entity in the triplet. The predefined characteristic relation may be applied to the output of the function, for example, whether or not the output of the function X+Y−Z is between zero and 10. In another example, the real tuplet includes entities, where each entity is a set of values, for example, the first entity is {1,2,3} and the second entity is {2,3,4}. The function calculates the largest value in the set of the entity, for example, the value for the first entity is 3 and for the second entity 4. The characteristic relation compares whether the output of the function applied to the first entity is larger than the value of the function applied to the second entity, whether 3 is greater than 4, which is FALSE.

The predefined characteristic relation may be applied between real tuplets of entities of two or more different data instances of the subset. For example, the subset may include names of individuals as entities and/or as data instances, for example, the subset {Mr. John Smith, Mr. Jack Williams, and Mrs. Marie Lamb}. The characteristic may include one or more of the following: the name containing Mr. implies that the Gender is male, the name containing Mr. implies that the age is above 16, and the name containing Mrs. Implies that the Gender is female. The predefined characteristic may be applied as a comparison between the tuplet of the first two members of the subset. Since both names contain Mr., the predefined characteristic relation is TRUE. The predefined characteristic may be applied as a comparison between the tuplet of the last two members of the subset. Since one name contains Mr. and another name contains Mrs., the predefined characteristic relation is FALSE.

The predefined characteristic relation may be applied between one or more real tuplets of entities of the same data instance of the subset. For example, each data instance may include a first entity representing a name, and a second entity representing an age. For example, the subset {Mr. John Smith, 40; Mr. Jack Black 13}. Using the example of the predefined characteristic relation discussed above, when the name includes Mr. the implied age is above 16, the predefined characteristic relation may be applied between the tuplets of entities of the same data instance to check whether the result is TRUE or FALSE. For the first case, the age is 40, and the predefined characteristic relation outputs TRUE. For the second case, the age is 13, and the output is FALSE.

Optionally, the predefined characteristic relation is identified and/or associated with one or more combination functions. Each combination function is created by selecting a function group of building block functions adapted for processing the entities of the real tuplets. Members of the function group are combined to create a set of combination functions. Each combination function is created from two or more members of the function group. Additional details of creating combination functions are described, for example, with reference to U.S. patent application Ser. No. 14/595,394.

Optionally, the characteristic relation may be identified by applying each function (optionally each member of the set of combination functions, and/or other predefined functions) to each real tuplet to create a set of results. The set of results is analyzed to identify a correlation between the one or more members of the set of combination functions and a target variable for analysis of the real tuplet according to a correlation requirement. The characteristic relation is selected based on the identified member of the set of combination functions. For example, the correlation requirement may define the statistical similarity of the values outputted by the combination function when applied to each entity of the tuple, for example, as a threshold or range, for example, 100% match, or a statistical correlation of at least 0.9, or other methods. In such a case, the characteristic relation may be an equality comparison when the combination function is applied to each entity of the tuple. In another example, the correlation requirement may define the statistical difference between the values. In such a case, the characteristic relation may be inequality, or greater than or less than. Additional details of automatically identifying characteristic relations (i.e., pivotal classification features) are described, for example, with reference to U.S. Patent Application No. 62/193,196.

Optionally, the predefined characteristic relation(s) is automatically selected from a set of predefined characteristic relations, based on a correlation between a first value calculated by applying each predefined characteristic relation of the set to a first real tuple, and one or more second values calculated by applying the same predefined characteristic relation to one or more other real tuplets, according to a correlation requirement representing the ability of the characteristic relation to identifying both first and second real tuplets (e.g., a range or threshold, for example at least 0.9, or at least 0.8, or a 100% match). For example, when the predefined characteristic relation is applied to the tuplets the same or similar result is obtained (according to the correlation requirement), the certain predefined characteristic relation may be selected. In another example, when the predefined characteristic relation is applied to the tuplets different results are obtained (according to the correlation requirement), the certain predefined characteristic relation may be rejected.

Optionally, at 107, one or more of the automatically predefined characteristic relations are presented to a user, for example, within a GUI presented on a display (e.g., user interface 218). The user (e.g., a specialist in the domain) may manually mark (e.g., using a touch-screen, a mouse, or a keyboard implementation of user interface 218) significant and/or relevant characteristic relations to the problem being addressed and/or to the problem domain. The marked characteristic relations are stored for calculation of the classifier, as described herein. Alternatively or additionally, the user may manually mark errors, insignificant, and/or irrelevant characteristic relations to the problem being addressed and/or to the problem domain. The irrelevant characteristic relations may represent statistically significant relations, but may actually be irrelevant to the domain problem at hand. The marked characteristic relations are removed from the set of identified predefined characteristic relations, and not used for calculation of the classifier. Marking may be performed, for example, by clicking the respective characteristic relations on the display.

The predefined characteristic relations (e.g., the manually selected characteristic relations) may be outputted and used to identify normal entities and/or anomalous entities in the dataset, and/or in a newly received dataset (and/or newly received data instances).

At 110, a classifier is calculated according to an analysis of the one or more dummy tuplets and one or more real tuplets. The real tuplets represent real data, and may be tagged as normal, or real. The real data is assumed to be normal data based on the assumption that the presence of any anomalous entities is statistically insignificant. The dummy tuplets represent anomalous data, and may be tagged as anomalous, or fake. The creation of the dummy tuplets artificially increases the proportion of anomalous data to reach a statistically significant level, which allows calculation of a classifier that is able to differentiate between normal and anomalous data with improved statistical significance.

Optionally, the proportion between real tuplets and dummy tuplets is selectable, for example, manually entered by the user using an interface, automatically calculated by code (e.g., based on a statistically significant target for the classifier), and/or retried from a storage of system configuration parameters. The proportion may be, for example, 1:1, 2:1, 1:2, or other values. When the number of created dummy tuplets is equal (or approximately equal to) the number of real tuplets, a proportion of less than 1:1 may be reached, for example, by randomly (or statistically sampling, or other methods) selecting a subset of the dummy tuplets to use to calculate the classifier, for example, 50% of the dummy tuplets, resulting in a proportion of 2:1 (real: dummy).

The dummy tuplets may be labeled with the calculated anomalous entity score. The calculated classifier may output a statistical probability of the anomalous entity score, and/or may detect anomalous entities with an associated calculated anomalous entity score.

Optionally, the analysis for calculating the classifier includes extracting feature-values from each of the dummy tuplets and each of the real tuplets. The feature-values may be extracted by applying the respective selected functions (e.g., combination functions) and/or calculating the respective predefined characteristic relations.

Optionally, a set of predefined characteristic relation(s) is selected for calculating the classifier based on the ability of each of the predefined characteristic relations to statistically distinguish between the real tuplet and the dummy tuplet according to a distinguishing requirement, for example, a correlation threshold and/or range. The set of predefined characteristic relations may be reduced by selecting the most statistically significant characteristic relations that are best able to differentiate between real data and dummy data (i.e., normal values and anomalous entities). The reduction in size of the set of predefined characteristic relations may improve computations performance of the computing unit.

Optionally, the identified predefined characteristic relation(s) are applied to the real tuplets to extract a first set of features representing real-feature-values (e.g., normal values). The same (or corresponding) identified predefined characteristic relation(s) are applied to the dummy tuplets to extract a second set of features representing dummy-feature-values representing anomalous entities. The classifier is calculated according to first set and the second set.

Alternatively or additionally, the identified redefined characteristic is applied to the one or more entities of the dummy tuple(s) and to one or more entities of the real tuple(s), to extract the second set (or a third set) for training the classifier.

The classifier may be calculated based on a created second data set that includes entities from the original dataset that were not processed by the permutation function, and corresponding entities outputted by the permutation function. Each data instance.

Optionally, another (e.g., second) dataset is created based on the original dataset and the permuted entities. The second dataset includes data instances having both original entities and dummy entities (i.e., permuted entities from another data instance). The data instances of the second dataset represent anomalous entities. The classifier is calculated according to an analysis of the real data instances of the original data set and the dummy (i.e. anomalous) data instances of the second dataset.

Optionally, an anomalous entity sub-score is calculated for each of the dummy tuplets. The dummy tuplet may include all dummy entities, or some real entities and some dummy entities. The anomalous entity sub-score may be a value (absolute or relative) indicative of the degree of anomalous entity of the dummy tuple.

The anomalous entity sub-score may be calculated, for example, based on the calculated correlation for the entities of the dummy tuplets, optionally based on the predefined characteristic relation. For example, a low correlation may represent a high degree of anomalous entity. In the case of higher number tuplets, for example, triplets, quadruplets, the calculated correlation may be calculated for tuplets of the triplets, or for all members of the triplets. In such a case, some entities may be anomalous entities, and some may not be anomalous entities, as reflected by the correlation and/or anomalous entity score.

The anomalous entity sub-score may be calculated based on the correlation when the selected function (e.g., combination function) is applied to each respective dummy tuplet in view of the characteristic relation.

An anomalous score may be calculated for the dummy data instances (which include one or more dummy tuplets) by aggregating (e.g., summing) the sub-scores of the dummy tuplets. In this manner, the calculated classifier (as described herein) may determine the data instances most likely to be anomalies based on the highest calculated anomaly scores.

Optionally, at 112, one or more blocks 104-110 are iterated to obtain additional data samples for calculating the classifier. The additional data samples may improve the accuracy of the classifier to detect anomalous entities. The iterations may be performed until a stop condition is met, for example the accuracy of the classifier in detecting anomalous entities reaches a statistical requirement (e.g., threshold, range).

Block 105 may be iterated to apply the permutation function on other entities from the dataset. Optionally, real tuplets of the subset are constraint at each iteration by applying a set-of-rules. The permutation function is applied according to the set-of-rules to respect the constraint to determine the dummy tuplets.

The set-of-rules may define two or more real entities included the in the real tuplets which retain their relative positions within the real tuplets. The two or more real entities are permuted together by the applied permutation function. For example, for a set of blood tests results, the set-of-rules may define that Hemoglobin and Hematocrit always remain together, either in the real tuplets or are permuted together to create dummy tuplets.

Block 106 may be iterated to identify other characteristic relations. Optionally, second order (or higher) characteristic relations may be identified as characteristic relations between previously identified characteristic relations.

The identified characteristic relation at each iteration may be stored (e.g., in a data repository). The set-of-rules applied in the next iteration may include one or more of the stored characteristic relations. The permutation function is applied while retaining the stored identified characteristic relation. For example, for a set of blood tests, if a relationship is found between two blood components, the permutation function is applied to retain the relationship.

Block 107 may be iterated to manually select relevant characteristic relations.

Block 110 may be iterated to update the calculated classifier based on the new data, and/or calculate the classifier based on the data collected from the iterations.

At 114, the classifier is used to detect one or more anomalous entities and/or normal entities in the original dataset and/or in another dataset. The classifier may output an indication of the level of accuracy that the identified entity represents an anomalous entity, for example, based on the calculated anomalous entity score, and/or other statistical methods. Alternatively or additionally, one or more of the identified characteristic relations are used to identify anomalous and/or normal entities in the dataset and/or in another dataset.

Optionally, the anomalies are presented to a user, for example, on a display (e.g., user interface 218). The user (e.g., a specialist in the domain) may manually mark significant anomalies and/or mark irrelevant anomalies, for example, by clicking the anomalies on the display. The irrelevant anomalies may represent statistically significant correlations, but may actually be irrelevant to the domain problem at hand. The manual markings may be used as feedback to the calculated classifier, for example, to prevent detection of the irrelevant anomalies in the dataset.

Reference is now made to FIG. 1B, which is a flowchart of a process that automatically identifies characteristic relation(s) of the dataset, in accordance with some embodiments of the present invention. The method identifies characteristic relations and/or functions (e.g., combination functions) within the dataset. The characteristic relations and/or functions may be statistically significant (e.g., according to a statistical requirement) for identification of anomalies. For example, in a dataset of medical records for patients, where each data instance stores multiple different lab measurements, the method may identify that that a characteristic relation between a random blood sugar level and hemoglobin (Hg) level is statistically significant to identify anomalous entities.

The method described with reference to FIG. 1B is an implementation based on the method described with FIG. 1A. For clarity and simplicity, the differences between the methods will be discussed. The system described with reference to FIG. 2 may implement the acts of the method of FIG. 1B.

At 152, dataset(s) are received, for example, as described with reference to block 102 of FIG. 1A.

At 154, a subset of training data instances is selected from the dataset and designated as real data, for example, by random sampling of the dataset, based on a statistical sampling method, based on an order of the dataset, manually selected by a user, or other methods, for example, as described with reference to block 104 of FIG. 1A.

At 156, another subset of training data instances is selected from the dataset for creation of dummy data. The other subset may be the same subset as in block 154, a subset of the subset of block 154, and/or selected from the original dataset(s) of block 152.

Dummy data is created by applying the permutation function to a tuplet (e.g., pair or columns) of the subset of training instances, for example, as described with reference to block 105 of FIG. 1A.

At 158, a tuplet (e.g. pair, triplet of columns) is selected for analysis using the real data and the dummy data. The tuplet may be selected, for example, iteratively to cover every possible permutation of columns, and/or statistically sampled to select a representative sample (to reduce computations instead of covering every possible permutation). For example, where there are three columns, there are 3 ways of selecting a pair of columns from the three columns, and 1 way of selecting all columns, for a total of 4.

At 160, one or more predefined characteristic relations and/or functions (e.g., combination functions) are identified for the selected tuplet of data. The predefined characteristic relations and/or functions may be identified based on statistically significant (e.g., according to a statistical requirement) ability to differentiate between normal and anomalous entities. For example, using the example of blood sugar and Hg, the predefined characteristic relation may differentiate between normal blood sugar and Hg and anomalous blood sugar and Hg.

Methods for identifying the characteristics relations and/or functions are described, for example, with reference to block 106 of FIG. 1A.

At 162, the identified characteristic relations may be presented to a user for manual intervention, optionally to designate the characteristic relation as relevant to the domain problem or irrelevant (i.e., even when the characteristic relation is statistically significant, the relation itself may be meaningless to the domain problem being addressed), for example, as described with reference to block 107 of FIG. 1A.

Optionally, at 164, one or more of blocks 158-162 are iterated. The iteration may be performed on every (or subgroup of, optionally based on statistical sampling methods) combination or permutation of data entities (e.g., columns) to identify characteristic relations. The characteristic relations may be presented in block 162 to the user as they are identified, or once a set or all relations are identified (e.g., iterate blocks 158-160).

At 166, the characteristic relations are used to identify anomalous entities in the existing dataset and/or for new data instances. The characteristic relation applied to entries of the data instance may identify anomalous entries, for example, applying the characteristic relation between blood sugar and Hg in existing and/or new medical records to identify anomalous entities.

Reference is now made to FIG. 1C is a flowchart of a process that automatically calculates a classifier and/or identifies characteristic relations of the dataset for identifying anomalous entities, in accordance with some embodiments of the present invention. The method trains a statistical classifier based on the identified characteristic relations and/or functions (e.g., combination functions) to identify anomalous data instances within the dataset and/or new data instances. Optionally, the characteristic relations and/or functions that are able to statistically significantly separate real and anomalous data are identified. The classifier may accept the characteristic relations and/or functions as input, for example, feature values may be extracted from the entities using the characteristic relations and/or functions.

The method described with reference to FIG. 1C is an implementation based on the method described with FIG. 1B and FIG. 1A. For clarity and simplicity, the differences between the methods will be discussed. The system described with reference to FIG. 2 may implement the acts of the method of FIG. 1C.

Blocks 152-160 are as described with reference to FIG. 1B.

At 170, a classifier is calculated for separating real data instances from dummy data instances based on the real subset of data and the dummy subset of data. The classifier identifies anomalous data within the existing dataset(s) and/or identifies new data instance(s) as real or anomalous. The classifier may be calculated using feature-values extracted from the real and/or dummy data using the identified characteristic relations and/or functions. Calculation of the classifier may be performed, for example, as described with reference to block 110 of FIG. 1A.

At 172, the calculated classifier and/or the identified characteristic relations and/or functions used to extract feature values for training and/or using the classifier may be presented to a user for manual intervention, optionally to designate the feature-value (and/or the characteristic relation and/or function used to extract the feature-value) as relevant to the domain problem or irrelevant (i.e., even when the characteristic relation is statistically significant, the relation itself may be meaningless to the domain problem being addressed), for example, as described with reference to block 107 of FIG. 1A.

Optionally, at 174, one or more of blocks 158, 160, 170, and 172 are iterated. The iteration may be performed on every (or subgroup of, optionally based on statistical sampling methods) combination or permutation of data entities (e.g., columns) to identify characteristic relations and/or functions. The classifier may be calculated (and/or updated)

using the identified characteristic relations and/or functions. The characteristic relations and/or functions may be presented in block 172 to the user as they are identified, or once a set or all relations are identified (e.g., iterate blocks 158-160).

At 176, the calculated classifier and/or characteristic relations and/or functions are used to identify anomalous entities in the existing dataset and/or for new data instances. The characteristic relations and/or function may be applied to entries of the data instance to extract feature-values. The features-values may be provided as input to the classifier to identify anomalous data instances, for example, in existing and/or new medical records to identify patients with anomalous data which may indicate disease.

An example based on the systems and/or methods described here is now described. Table 1 below represents an original dataset, in which entities are organized in two rows, W and V. Each row may represent a data instance.

TABLE 1

| W | V |
|---|---|
| artifact | alas |
| boy | barbi |
| car | cow |
| dove | dig |
| done | zebra |

A permutation function is applied to column V to create a column V'. A second dataset representing dummy data (e.g., anomalous entities) is created by associating the permuted entities of V' with the original entities of column W. The original dataset is tagged with a real label (e.g., by adding a third Label column). The created dataset is tagged with a dummy label. Table 2 below shows the original dataset (the first 5 rows) concatenated with the second dataset (the last 5 rows) including the Label column. The classifier is calculated using the data of Table 2. The features of the classifier may include functions (e.g., composition functions), for example, f(a,b)=charactersIn(a).head==charactersIn(b).head.

TABLE 2

| A | B | Label |
|---|---|---|
| artifact | alas | real |
| boy | barbi | real |
| car | cow | real |
| dove | dig | real |
| done | zebra | real |
| artifact | cow | dummy |
| boy | alas | dummy |
| car | barbi | dummy |
| dove | zebra | dummy |
| done | dig | dummy |

Figure 3:
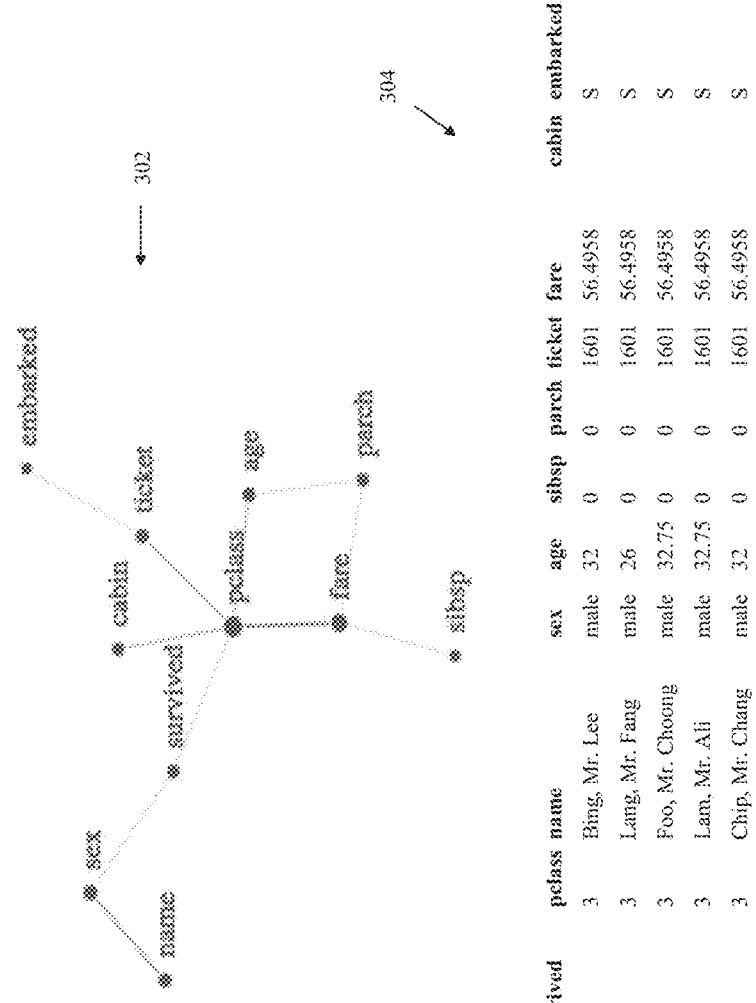
FIG. 3 includes a graph depicting identified characteristic relations and a table of identified anomalous data instances based on execution of the method of FIGS. 1A-C and/or the system of FIG. 2 on a publicly available dataset of Titanic passengers, in accordance with some embodiments of the present invention.

In another example based on the systems and/or methods described herein, the dataset is a publicly available dataset that includes details of the survivors of the Titanic. The dataset was analyzed based on the systems and/or methods described herein. Graph 302 shown in FIG. 3 represents identified characteristic relations between entities of the dataset. The entities are represented as nodes (shown as circles). The characteristic relations are shown as lines between the nodes. The correlation between entities based on the characteristic relation may be represented by the thickness of the line connecting the entities, with thicker lines representing higher correlation values. Table 304 includes entities and/or data instances identified as anomalous entities by the classifier calculated for the Titanic dataset based on the systems and/or methods described herein. Each anomalous entity data instance represents a survivor. Each data instance may be associated with an anomalous entity score.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant datasets and classifiers will be developed and the scope of the terms dataset and classifier are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer-implemented method of identifying anomalous entities in a dataset, comprising:
    using at least one hardware processor for executing a code for:
        selecting a subset stored in a hardware storage unit and comprising a plurality of training entities from a plurality of entities of at least one dataset;
        determining a plurality of dummy tuplets of entities in the subset by applying a permutation function on a plurality of real tuplets, wherein the real tuplets represent original and normal data of the at least one dataset, wherein the dummy tuplets represent anomalous data based on artificially created data not found in the original and normal at least one dataset, each one of the plurality of real tuplets and dummy tuplets comprises at least two of the plurality of training entities;
        analyzing the plurality of dummy tuplets and the plurality of real tuplets to identify at least one predefined characteristic relation that statistically differentiates between the real tuplets and the dummy tuplets according to a distinguishing requirement; and
        identifying, according to the identified at least one predefined characteristic relation, at least one of a normal entity and an anomalous entity in the at least one dataset or in a newly received dataset.

2. The computer-implemented method of claim 1, further comprising:
    calculating a first classifier that identifies the at least one predefined characteristic relation that statistically differentiates between an anomalous entity and a normal entity; and
    calculating a second classifier for detecting at least one of an anomalous entity and a normal entity in the at least one dataset or in the newly received dataset based on the at least one predefined characteristic relation identified by the first classifier.

3. The computer-implemented method of claim 1, wherein the plurality of training entities represent certain values assigned to variables, wherein each of the real tuplets comprises a tuplet of variables.

4. The computer-implemented method of claim 3, wherein the dataset includes a plurality of data instance each associated with at least one of the parameters having assigned values represented as entities, wherein each of the real tuplets comprises at least two different parameters.

5. The computer-implemented method of claim 1, wherein the dataset includes a plurality of data instances each including at least one entity, wherein the dataset is represented as a table, wherein each row of the table represents a respective data instance and each column of the table represents a respective entity, wherein the real tuplets includes at least two columns of the table.

6. The computer-implemented method of claim 5, wherein the dataset comprises raw data that includes normal data instances and unknown anomalous data instances.

7. The computer-implemented method of claim 5, wherein the permutation function is applied to at least one columns of the table to permute the entities of the rows of the column, such that the dummy tuplets includes for each row at least original entity and at least one permuted entity.

8. The computer-implemented method of claim 1, wherein the permutation function samples entities from the entities of the real tuplets according to a proportion requirement defining the proportion of real pairs to dummy pairs.

9. The computer-implemented method of claim 1, wherein the training entities include objects of arbitrary types.

10. The method of claim 9, wherein the arbitrary types are members selected from a set consisting of: time series, vector, map, graph, text, and tree.

11. The computer-implemented method of claim 1, wherein the training entities include complex data structures storing multiple parameters.

12. The computer-implemented method of claim 1, wherein the predefined characteristic relation is associated with values outputted by at least one function that processes each entity of the real tuplets.

13. The computer-implemented method of claim 1, wherein the predefined characteristic relation is identified based on at least one combination function created by selecting a function group of building block functions adapted for processing the entities of the real tuplets, and combining members of the function group to create a set of combination functions each created from at least two members of the function group.

14. The computer-implemented method of claim 13, further comprising selecting the characteristic relation by: applying each member of the set of combination functions to each real tuplet to create a set of results, analyzing the set of results to identify a correlation between the at least one member of the set of combination functions and a target variable for analysis of the real tuplets according to a correlation requirement, wherein the characteristic relation is selected based on the identified at least one member of the set of combination functions.

15. The computer-implemented method of claim 1, wherein analyzing comprises applying a function to extract dummy feature-values from each of the plurality of dummy tuplets and real feature-values each of the plurality of real tuplets, and applying a classifier to statistically differentiate between the dummy feature-values and the real feature-values to identify the at least one characteristic relation.

16. The computer-implemented method of claim 1, further comprising:
    applying each of a plurality of predefined characteristic relations to the real tuplets to extract a first set of features representing real-feature-values;
    applying each of the plurality of predefined characteristic relation to the dummy tuplets to extract a second set of features representing dummy-feature-values representing anomalous entities; and
    identifying the at least one predefined characteristic relation that statistically differentiates between the first set and the second set.

17. The computer-implemented method of claim 1, further comprising calculating an anomalous entity sub-score for each of the dummy tuplets based on the identified at least one predefined characteristic relation applied to each respective dummy tuple, and calculating an anomalous score for an identified anomalous data entity by aggregating sub-scores of dummy tuplets associated with the respective anomalous data entity.

18. The computer-implemented method of claim 1, further comprising:
    applying the identified at least one predefined characteristic to the real tuplets to extract a first set of features representing real-feature-values;
    applying the identified at least one predefined characteristic to the at least one entity of the dummy tuplets and to at least one entity of the real tuplets, to extract a second set of features representing dummy-feature-values representing anomalous entities; and
    calculating a classifier to identify at least one of a normal entity and an anomalous entity according to first set and the second set.

19. The computer-implemented method of claim 1, wherein the permutation function is a random permutation function.

20. The computer-implemented method of claim 1, wherein the permutation function is based on a predefined statistical distribution designed to capture a representative permutation sample to reduce computations resources as compared to computing all possible permutations.

21. The computer-implemented method of claim 1, further comprising iterating the determining and the analyzing by constraining a plurality of real tuplets of the subset at each iteration by applying a set-of-rules, and applying the permutation function according to the set-of-rules to respect the constraining to determine the plurality of dummy tuplets.

22. The computer-implemented method of claim 21, further comprising storing the at least one identified characteristic relation for each iteration, and wherein the set-of-rules applied in a next iteration include the identified at least one characteristic such that applying the permutation function according to the set-of-rules retains the stored at least one identified characteristic relation.

23. The computer-implemented method of claim 21, wherein the set-of-rules defines at least two real entities included the in the plurality of real tuplets which retain their relative positions, such that the at least two real entities are permuted together by the applied permutation function.

24. The computer-implemented method of claim 1, wherein the subset is selected according to a statistical estimate based on an estimated amount of anomalous entities in the at least one dataset such that applying the identified at least one predefined characteristic relation to each pair of the plurality of real tuplets is statistically significant according to a correlation requirement.

25. The computer-implemented method of claim 1, wherein the at least one predefined characteristic relation is applied between real tuplets of entities of the same data instance of the subset.

26. The computer-implemented method of claim 1, wherein the at least one predefined characteristic relation is selected by:
    applying a function to each real tuplets to calculate a set of first results;
    generating a set of characteristic relations wherein each characteristic relation includes the function for application to another real tuplets to calculate a second result, and at least one condition defined by at least one respective member of the set of first results applied to the second result;
    applying each characteristic relation of the generated set of characteristic relations to each instance of a second subset selected from the at least one dataset to generate a set of extracted features;
    selecting a subset of characteristic relations from the set of characteristic relations according to a correlation requirement between at least one classification variable and each respective member of the set of characteristic relations; and
    designating the selected subset of characteristic relations at the identified at least one predefined characteristic relation.

27. The computer-implemented method of claim 1, further comprising:
    receiving a manual selection of said at least the presented predefined characteristic relations from said user via said user interface.

28. The computer-implemented method of claim 1, wherein said at least one hardware processor is further used for presenting a user interface and for receiving a user input related to said at least one predefined characteristic relation from a user via said user interface;
    wherein said at least one of a normal entity and an anomalous entity is identified using said user input.

29. The computer-implemented method of claim 1, wherein said at least one hardware processor is further used for instructing a presentation of said at least one of a normal entity and an anomalous entity on a display.

30. A system for identifying anomalous entities in a dataset, comprising:
    a data interface for communicating with a storage unit storing thereon at least one dataset;
    a program store storing code; and
    a processor coupled to the data interface and the program store for implementing the stored code, the code comprising:
        code to access said storage unit and to select a subset comprising a plurality of training entities from a plurality of entities of at least one dataset;
        code to determine a plurality of dummy tuplets of entities in the subset by applying a permutation function on a plurality of real tuplets, wherein the real tuplets represent original and normal data of the at least one dataset, wherein the dummy tuplets represent anomalous data based on artificially created data not found in the original and normal at least one dataset, each one of the plurality of real tuplets and dummy tuplets comprises at least two of the plurality of training entities;

code to analyze the plurality of dummy tuplets and the plurality of real tuplets to identify at least one predefined characteristic relation that statistically differentiates between the real tuplets and the dummy tuplets according to a distinguishing requirement; and code to identify at least one of a normal entity and an anomalous entity in the at least one dataset or in a newly received dataset according to said at least one predefined characteristic relation.

31. A computer program product comprising a non-transitory computer readable storage medium storing program code thereon for implementation by a processor of a system for identifying anomalous entities in a dataset, comprising:

instructions to access a storage unit and to select a subset comprising a plurality of training entities from a plurality of entities of at least one dataset stored in said storage unit;

instructions to determine a plurality of dummy tuplets of entities in the subset by applying a permutation function on a plurality of real tuplets, wherein the real tuplets represent original and normal data of the at least one dataset, wherein the dummy tuplets represent anomalous data based on artificially created data not found in the original and normal at least one dataset, each one of the plurality of real tuplets and dummy tuplets comprises at least two of the plurality of training entities;

instructions to analyze the plurality of dummy tuplets and the plurality of real tuplets to identify at least one predefined characteristic relation that statistically differentiates between the real tuplets and the dummy tuplets according to a distinguishing requirement; and instructions to identify at least one of a normal entity and an anomalous entity in the at least one dataset or in a newly received dataset according to said at least one predefined characteristic relation.

* * * * *